US005327895A

United States Patent [19]

Hashimoto et al.

[11] Patent Number: 5,327,895

[45] Date of Patent: Jul. 12, 1994

[54] ULTRASONIC PROBE AND ULTRASONIC DIAGNOSING SYSTEM USING ULTRASONIC PROBE

[75] Inventors: Shinichi Hashimoto; Shiroh Saitoh; Mamoru Izumi, all of Tokyo, Japan

[73] Assignee: Kabushiki Kaisha Toshiba, Kanagawa, Japan

[21] Appl. No.: 901,107

[22] Filed: Jun. 19, 1992

[30] Foreign Application Priority Data

Jul. 10, 1991 [JP] Japan .................................. 3-170114

[51] Int. Cl.[5] .............................................. A61B 8/00

[52] U.S. Cl. ............................... 128/662.03; 310/334; 29/25.35

[58] Field of Search ........................ 128/661.1, 662.03; 73/625-626; 310/334; 29/25.35

[56] References Cited

U.S. PATENT DOCUMENTS

| | | | |
|---|---|---|---|
| 4,640,291 | 2/1987 | t'Hoen | 128/662.03 |
| 4,671,293 | 6/1987 | Shaulov | 128/662.03 X |
| 4,939,826 | 7/1990 | Shoup | 29/25.35 |
| 5,097,709 | 3/1992 | Masuzawa et al. | 128/661.01 X |
| 5,099,459 | 3/1992 | Smith | 128/662.03 X |
| 5,122,993 | 6/1992 | Hikita et al. | 128/662.03 X |
| 5,164,920 | 11/1992 | Bast et al. | 128/662.03 X |

FOREIGN PATENT DOCUMENTS

| | | |
|---|---|---|
| 57-68999(A) | 4/1982 | Japan . |
| 57-68999 | 4/1982 | Japan . |
| 60-086999 | 5/1985 | Japan . |
| 62-5337 | 1/1987 | Japan . |

*Primary Examiner*—Francis Jaworski
*Attorney, Agent, or Firm*—Finnegan, Henderson, Farabow, Garrett & Dunner

[57] ABSTRACT

An ultrasonic diagnosing system includes a probe having an vibrator made of a plurality of spaced piezoelectric; material elements arranged in a matrix, first electrodes arranged on one surface of the vibrator in an array of rows parallel to each other, and second electrodes arranged on another surface of the vibrator in an array of rows parallel to each other and orthogonally to the first electrodes.

Particularly, the piezoelectric material elements are spaced by spacer segments arranged between the electrode rows and formed from a high molecular weight material with less acoustic impedance than the piezoelectric material, a Shore hardness D50 or more (JIS) and a thickness of about 1/10 to ½ of the piezoelectric elements. The ultrasonic diagnosing system uses a phased array technique to provide tomograms at mutually orthogonal and spatially close positions with sufficient sensitivity.

22 Claims, 7 Drawing Sheets

ULTRASONIC PROBE AND ULTRASONIC DIAGNOSING SYSTEM USING ULTRASONIC PROBE

BACKGROUND OF THE INVENTION

Field of the Invention

The present invention relates to an ultrasonic probe and an ultrasonic diagnosing system using this ultrasonic probe, in particular, an ultrasonic prone capable of observing two orthogonal cross sections, and an ultrasonic diagnosing system using this ultrasonic probe.

Description of the Related Art

In medical diagnosis, it is known to display a tomogram of a part of a subject on a display unit and observe it. An ultrasonic diagnosing system is used to obtain the tomogram.

In non-destructive testing of structural materials, etc., an ultrasonic flaw detecting system can be used.

Conventional ultrasonic medical diagnosing systems and ultrasonic flaw detecting systems are equipped with ultrasonic probe having a vibrator made of such piezoelectric material as lead titanate zirconate (PZT) and two electrodes arranged on opposing vibrator surfaces. The medical diagnosing systems obtain a tomogram by scanning this ultrasonic probe mechanically or providing an ultrasonic probe having a structure wherein multiple vibrators are arranged in arrays, and applying electric pulses to the arrays after electrically delaying the arrays, to scan the ultrasonic beams to get a tomogram.

In recent years, to perform medical diagnosing via the esophagus or the rectum, in order for more accurate medical diagnosis, it has become desirable to observe one more tomograms at a position orthogonal and close to a tomogram of certain cross-sectional part of a subject, in addition to a tomogram of that position.

However, even if it is tried to provide two tomograms at positions orthogonal to each other by putting two ultrasonic probes side by side, the probes cannot be arranged exactly at the desired positions because of the required spacing between the ultrasonic probes. Therefore, observation of different parts of a subject can result. Further, if it is tried to observe two orthogonal tomograms by rotating the ultrasonic probe, accurate rotation of existing ultrasonic probes is difficult and complicated in the case where the ultrasonic probe is positioned in the inside of a subject, for instance, in the esophagus or the rectum. Furthermore, if the rotary mechanism is housed in the ultrasonic probe, an undue increase in the size of the ultrasonic probe, and increase in the subject's pain may result.

An ultrasonic probe capable of obtaining two orthogonal tomograms has been disclosed in Japanese Patent Disclosure TOKU-KAI-SHO No. 57-68999. This ultrasonic probe has a structure wherein both surfaces of the piezoelectric material member are machined or otherwise processed to have multiple grooves in orthogonal directions, and multiple electrodes are provided on the parts of the surfaces of the piezoelectric material divided by these grooves. The electrodes provided on one surface of the piezoelectric material are grounded.

The ultrasonic probe mentioned above is capable of observing two tomograms at the positions that are orthogonal and close to each other.

However, this ultrasonic probe has some limitations because it is necessary to switch the electrodes alternately to which electric pulses are applied in order to observe two tomograms.

Firstly, the piezoelectric material normally has a uniform direction of polarization, and it is the general practice to provide scanning ultrasonic beams by applying electric pulses in the same electric polarity as this direction of polarization. However, in the case of the system to switch electrodes alternately, the electric pulses may be applied in a polarity reverse to the direction of polarization, and so-called "depolarization" can result. Although this depolarization can be avoided by lowering the applied pulse voltage, the lower pulse voltages will make ultrasonic beam output lower and a tomogram at the desired sensitivity may not be obtained.

Secondly, conventional ultrasonic probes may have the defect wherein the electric pulse transmission/-receiving surface, that is, the surface to which electric pulses are applied, contacts the subject who may get an electric shock. If an insulation layer is provided to prevent the electric shock, the ultrasonic beam output may be lowered unacceptably.

Thirdly, on conventional ultrasonic probes, acoustic crosstalk can occur because the vibrators arranged in the array are not completely cut and physically divided but are partially connected. In such a case, the surface of each vibrator part not only directly transmits and receives ultrasonic waves but also indirectly transmits and receives other ultrasonic vibrations that are transmitted or received on the surface of other vibrator parts.

Furthermore, electric crosstalk tends to occur and together with the acoustic crosstalk, can lower the accuracy of a tomogram.

SUMMARY OF THE INVENTION

Accordingly, it is an object of the present invention to provide an ultrasonic probe and an ultrasonic diagnosing system using the ultrasonic probe capable of obtaining tomograms at mutually orthogonal and spatially close positions at high resolution and sensitivity.

In accordance with the present invention, as embodied and broadly described herein, there is provided an ultrasonic probe comprising a vibrator member comprising a plurality of spaced member elements of a piezoelectric material arranged in a matrix, each of the elements having front and back opposing surfaces. First electrode means are disposed on the front surfaces of the member elements, and second electrode means are disposed on the back surfaces of the member elements. A plurality of spacer segments are disposed between adjacent ones of the member elements, with the segments being formed of a high molecular weight material having an acoustic impedance less then that of the piezoelectric material. Preferably, the spacer segments occupy less than the total volume of space between the spaced member elements, and the volume of space not occupied by the spacer segments is filled with at least one filling material having an acoustic impedance of about 3 Mrayls or less and a Shore hardness of 40A (JIS) or less. It is further preferred that the thickness of the spacer segments in the front-back direction is between about 1/10–½ that of the member elements.

And it is still further preferred that the first and second electrode means includes a plurality of strip electrodes electrically interconnecting respective member elements in an array of parallel rows. The direction of the row array defined by the electrodes of the first electrode means is orthogonal to the row array direction defined by the electrodes of the second electrode means. Also, a matching layer, which can be in the form of matching layer elements, can be disposed over the front surfaces of the member elements, and an acoustic lens can be disposed over the matching layer.

Further in accordance with the present invention, there is also provided an ultrasonic diagnosing system comprising a vibrator made of piezoelectric material, a common electrode arranged on one surface of the vibrator, a matrix-shaped electrode arranged on the other surface of the vibrator, and a source of electric pulses to apply electric pulses to the electrodes. Switching means interconnecting the electrodes are capable of selecting between a first imaging position and a second imaging position. In the first imaging position, the switching means connects the matrix-shaped electrodes to the source, for example, by short circuiting them in one common direction (e.g., the vertical direction). In the second imaging position, the switching means connects the matrix-shaped electrode to the source, for example by short circuiting them, in the orthogonal direction, such as the horizontal direction.

Still further in accordance with the present invention, there is provided a method for making a vibrator member of an ultrasonic probe, the vibrator member comprised of a plurality of member elements each having opposing front and back surfaces and arranged in a matrix and spaced by spacer segments, a plurality of first electrodes disposed on the front surfaces of the member elements to form a first array of parallel rows of electrically interconnected member elements, a plurality of second electrodes disposed on the back surfaces of the member elements to form a second array of electrically interconnected member elements, the directions of the first and second arrays being mutually orthogonal. The method comprising the steps of arranging the member elements into the matrix; forming a high molecular weight material in the volume space between adjacent member elements; forming first and second electrode sheets covering the front and back surfaces respectively of the arranged member elements; removing both the portion of the first electrode sheet covering the high molecular weight material between the intended rows of the first array to form the first electrodes, and a portion of the high molecular weight material between the removed electrode sheet portion, the removed high molecular weight material portion extending to a depth less than the thickness of the member elements, thereby forming the spacer segments between the rows of the first array; and repeating the last-mentioned step but for the second electrode sheet to form the second electrodes and the spacer segments between the rows of the second array.

BRIEF DESCRIPTION OF THE DRAWINGS

These and other objects and advantages of this invention will become more apparent and more readily appreciated from the following detailed description of the presently preferred exemplary embodiments of the invention taken in conjunction with the accompanying drawings wherein.

DESCRIPTION OF THE PREFERRED EMBODIMENT

The embodiments of the ultrasonic diagnosing system of the present invention are explained hereinafter referring to the attached drawings. However, the present invention is not limited to the constructions shown in the figures.

Embodiment 1

Figure 1:
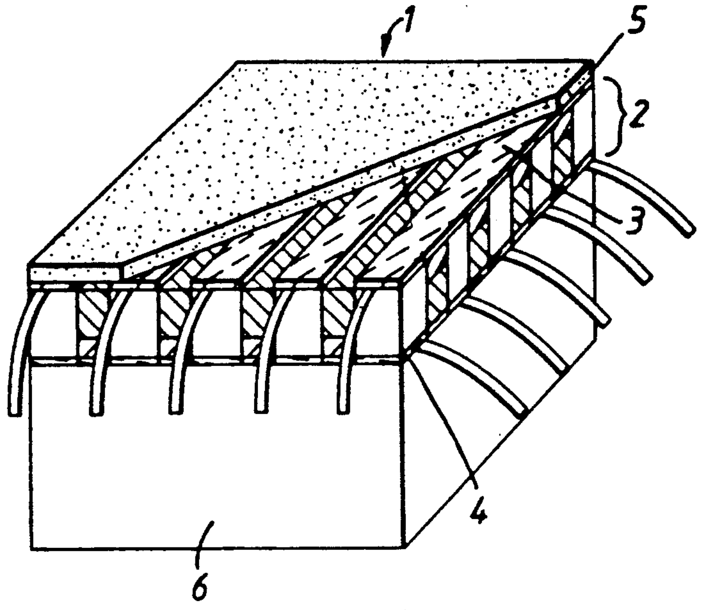
FIG. 1 is an oblique view showing an ultrasonic probe according to the present invention.

FIG. 1 shows schematically the construction of an ultrasonic probe 1 made in accordance with the present invention. This ultrasonic probe 1 includes a vibrator 2 made of a plurality of discrete, arrayed vibrator elements 2*a* of a piezoelectric material, electrodes 3 and 4 arranged on the front and back sides, respectively, of the vibrator 2 in multiple rows parallel to each other, a matching layer 5 arranged on the front side of the vibrator 2 and covering the electrodes 3, and backing material 6 arranged on the back side of the vibrator 2. The matching layer 5 transmits ultrasonic waves between vibrator 2 and a subject (not shown), while the backing material 6 absorbs ultrasonic waves vibrated toward the backside of the vibrator 2.

Figure 2A:
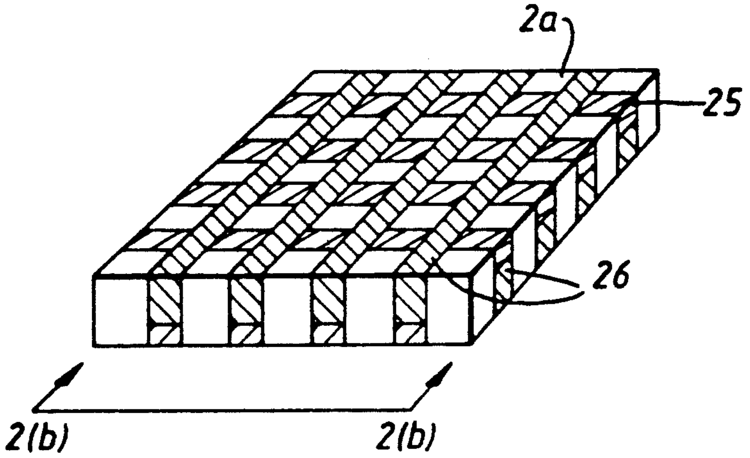
FIGS. 2(*a*) and (*b*) are partial oblique views showing the vibrating part of the ultrasonic probe drawn in FIG. 1.
Figure 2B:
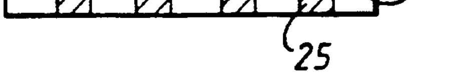
Figure 3A:
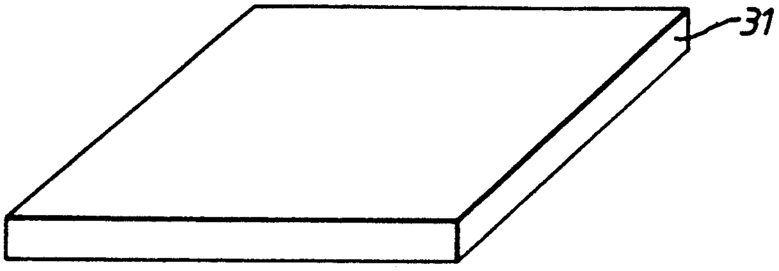
FIGS. 3(*a*) to (*h*) are stages in the construction of the ultrasonic probe showing in FIG. 1.
Figure 3B:
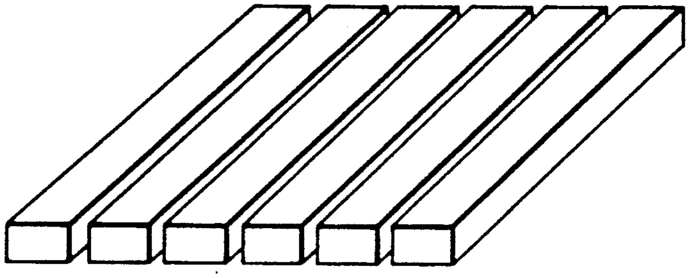
Figure 3C:
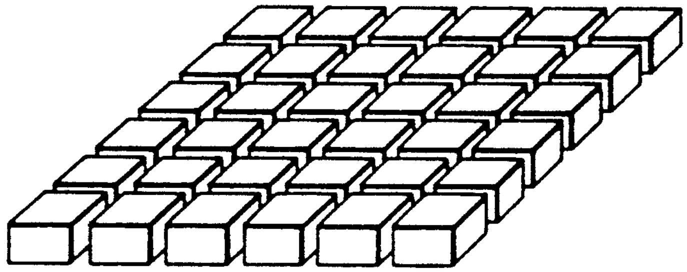
Figure 3D:
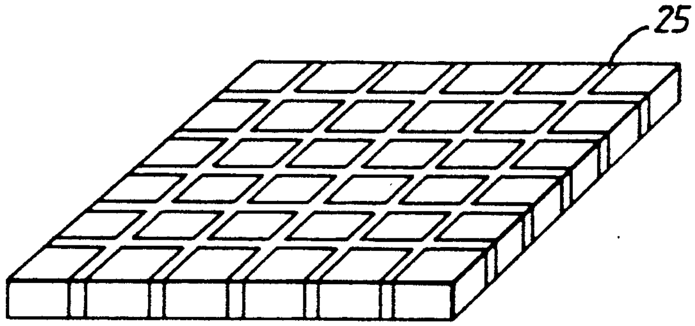
Figure 3E:
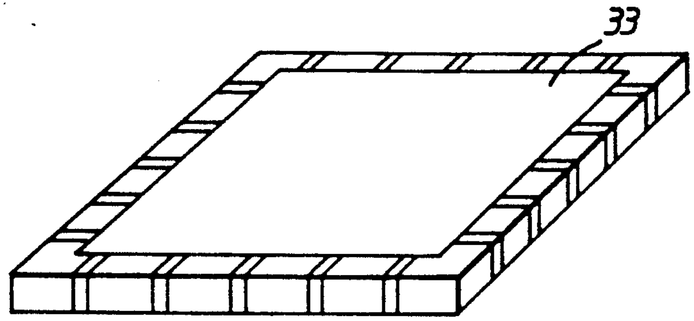
Figure 3F:
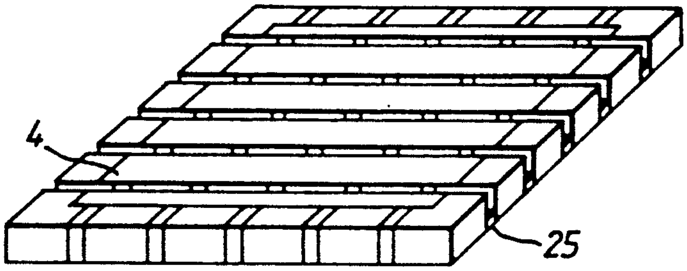
Figure 3G:
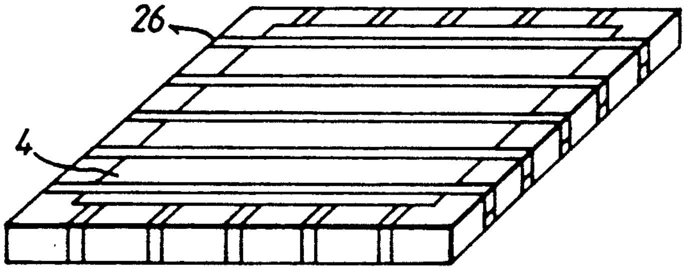
Figure 3H:
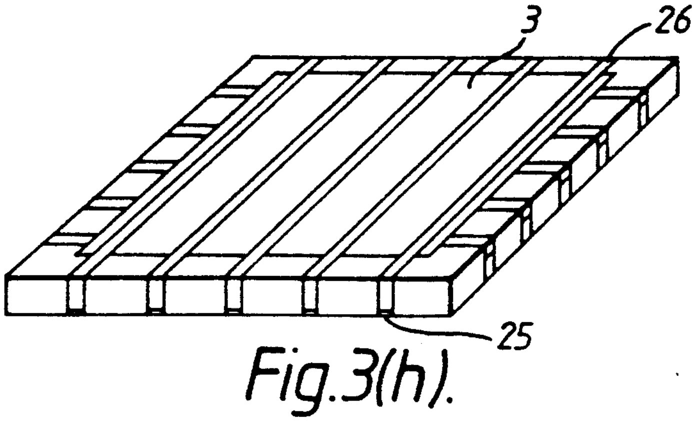

Shown in FIG. 2(*a*) is the ultrasonic probe 1 depicted without the electrodes 3 and 4, matching layer 5, and backing material 6. FIG. 2(*b*) is a side view (from 2(*b*)-2(*b*)-direction) of the ultrasonic probe shown in FIG. 2(*a*).

As seen in FIGS. 2(*a*) and 2(*b*), the vibrator elements 2*a* are arranged and held in a matrix shape by discrete spacer segments 25 interposed between the vibrator elements. The spacer segments 25 adjacent the front side of vibrator 2 are arranged to space the vibrator elements in the row direction of the electrodes 3, while the spacer segments 25 adjacent the back side of vibrator 2 are arranged to space the vibrator elements in the row directions of electrodes 4. Each of the spacer segments is formed of a high molecular weight material, has a thickness of about 1/10 to ½ of that of the vibrator 2, and exhibits above D50 of Shore hardness in JIS (Japan Industrial Standard). The open spaces of channels in the above-described vibrator matrix can be filled with filling material 26 having below A40 of Shore hardness in JIS and acoustic impedance less than 3 Mrayls. For this filling material, silicone resin is preferable. Below 2.5 Mrayls are more preferable, and the air may be used if a vibrator matrix having open channels or spaces can be tolerated in the probe.

The ultrasonic probe shown in this embodiment can be manufactured in the following manner, as shown in FIG. 3 (*a*) to (*h*).

First, a piezoelectric material 31 is cut into small cubeshaped elements and arranged in the matrix arrangement conforming to the array positions as shown in (a) to (c).

Second, the high molecular material for the spacer segments 25 is formed between the piezoelectric material cubes as shown in (d).

Third, layers 33 of the material for the electrodes 3 and 4 are formed on both sides of the piezoelectric material cubes and the high molecular material as shown in (e).

Fourth, grooves are made in the electrode material and in the high molecular material under the electrodes to form the array electrodes 4 and the spaced segments 25 adjacent the opposing matrix surface of the vibrator, as shown in (f).

Fifth, the grooves forming electrodes 4 are filled with filling material 26 as shown in (g).

Sixth, on the other side of the electrode material and the high molecular material the grooves forming electrodes 3 and the spacer segments adjacent the first matrix surface are also made but in a direction orthogonal to the grooves forming electrodes 4, and filled with filling material 26 as shown in (h).

The advantageous use of the ultrasonic probe 1 of this embodiment in the ultrasonic diagnosing system is explained hereunder.

Figure 4:
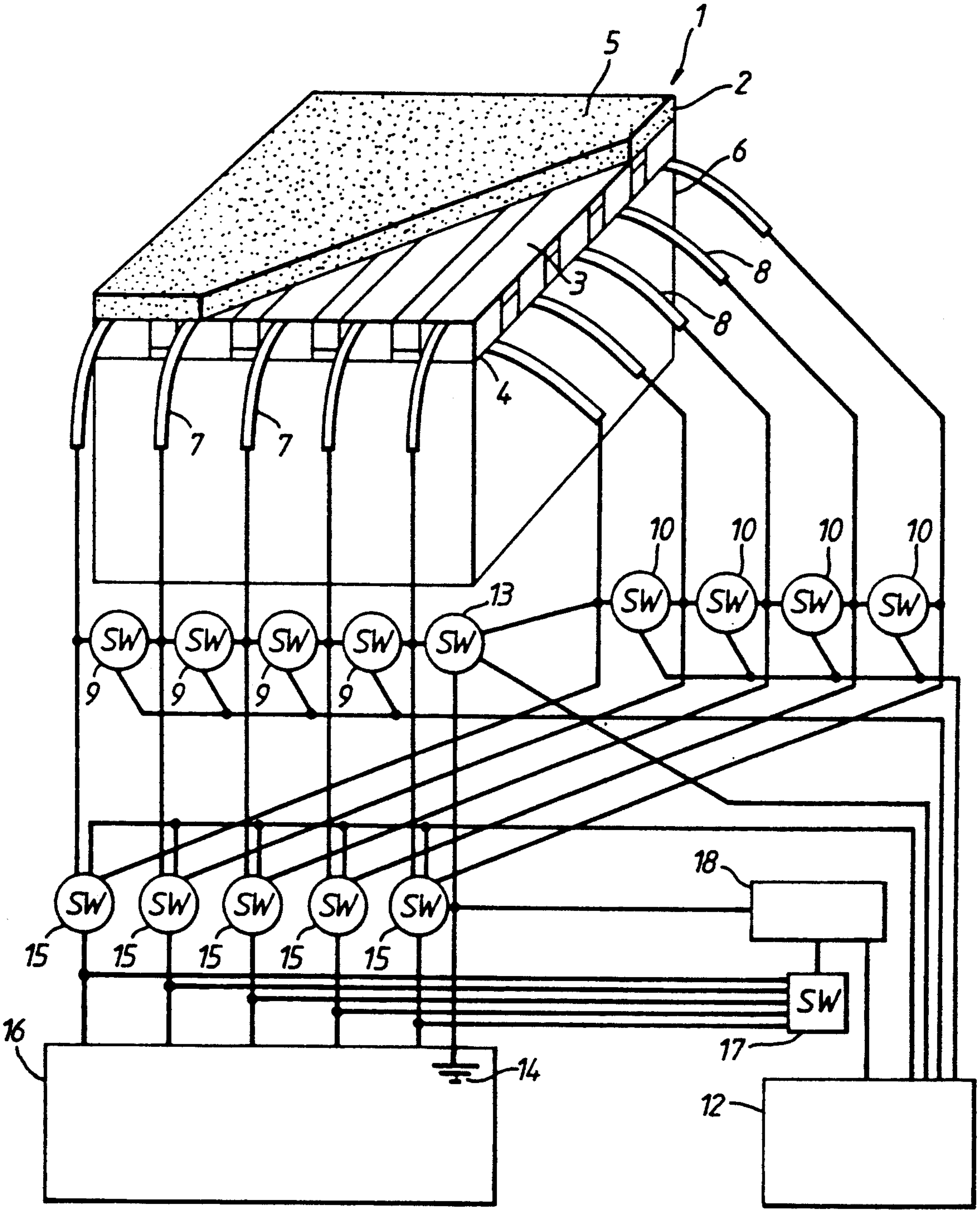
FIGS. 4 to 6 are oblique views showing another embodiment of the present invention.

FIG. 4 shows an ultrasonic diagnosing system in accordance with the present invention. This ultrasonic diagnosing system includes ultrasonic probe 1 that transmits and receives ultrasonic waves for examination of a subject. Ultrasonic probe 1 comprises vibrator 2 composed of piezoelectric material, the electrodes 3 and 4 arranged in several rows parallel to each other on the front and back sides of the vibrator 2, matching layer 5 covering the electrodes 3 arranged on the surface of the vibrator 2 and backing material 6 arranged on the back side of the vibrator 2. The electrodes 3 arranged on the front side of the vibrator 1 are arranged orthogonally to other electrodes 4 arranged on the back side. Further, the matching layer 5 functions to facilitate transmission of ultrasonic waves between the vibrator 2 and a subject while the backing material 6 functions to absorb ultrasonic waves vibrated to the back side of the vibrator 2.

The electrodes 3 of ultrasonic probe 1 are electrically connected to respective leads 7 which can be short-circuited to each other by the switch group 9. The electrodes 4 of the ultrasonic probe 1 are also electrically connected to respective leads 8 which can be short-circuited to each other by the switch group 10. The switch groups 9 and 10 are connected to the control unit 12 which is a control means and are driven and controlled by the signal from this control unit.

On the other hand, the switch groups 9 and 10 can be selectively grounded to the earth 14 via switch 13 that is controlled by the control unit 12 and thus ground either the short-circuited electrodes 3 or 4 by the switch 13.

The leads 7 from the electrodes 3 and the leads 8 from the electrodes 4 are selectively connected to pulser/receiver 16, that is, a source of electric pulses, via the switch group 15. The switch group 15, which applies driving pulses (electric pulses) from the pulser/receiver 16 to the electrodes 3 and 4, is controlled by the control unit 12.

To change the direction of polarization of the piezoelectric material of the vibrator 2, DC voltage is applied from the voltage source 18 between the electrodes 3 (or 4) short-circuited by the switch group 9 or 10 and the electrodes 4 (or 3) connected via the switch group 15 and the switch 17. The high-voltage source 18 is controlled by the control unit 12. The polarization process of the vibrator 2 is carried out by selecting the switches 9, 10, 13, 15 and 17 as necessary. Thereafter, to make the polarity of the electrodes 3 or 4 the same as that of the direction of polarization of the vibrator 2, electric pulses are applied to the appropriate electrodes 3 or 4 from the pulser/receiver 16 to generate ultrasonic waves.

To make the construction of the pulser/receiver 16 simple, the polarity of electric pulse output can be made constant in this embodiment. Therefore, depolarization can be avoided by selecting the electrodes to which electric pulses are applied after selecting the direction of polarization of the vibrator in advance according to the ultrasonic: wave scanning direction. However, as it is not necessary to change the direction of polarization of the vibrator by the source of high-voltage in advance if the pulser/ receiver selected is capable of outputting both positive and negative polarities. In such a construction, the polarity of electric pulses to be applied can be selected according to the ultrasonic scanning direction.

The operation of the ultrasonic diagnosing system will now be explained.

When providing scanning ultrasonic waves in the array direction of the electrode 3 of the vibrator 2 incorporated in the ultrasonic probe 1, namely, in a direction perpendicular to the row direction of electrodes 3, the switch group 9 is opened and the switch group 10 is closed to short circuit the electrode 4 and the switch 13 is closed to ground the electrode 4. Then, by closing the switch group 15, the pulser/receiver 16 is connected to the switch group 9 and then, by closing the switch 17, the source of high-voltage 18 is connected to the switch group 15 side. After polarizing the vibrator 2 by the source of high-voltage 18 under this state, the switch 17 is opened and the row-array of electrodes 3 at the switch group 9 side are driven by the pulser/ receiver 16.

When electric pulses are applied to each of the arrayed electrodes 3, the vibrator 2 generates ultrasonic waves which are turned to spherical waves and transmitted through a subject from each array. The pulser/-receiver 16 has the same number of channels as the number of arrays of the electrode 3 and is capable of applying electric pulses to each row of electrodes at fixed time intervals. Therefore, it is possible to focus ultrasonic waves to a fixed point in a subject corresponding to these time intervals, that is, electric delays. To focus ultrasonic waves to another point, it is required to apply electric pulses to the array electrodes 3 by applying electric delays corresponding to that point and thus, a tomogram of a subject in the array direction can be obtained.

When scanning ultrasonic waves in the array direction of the electrodes 4, namely, in a direction perpendicular to the row direction of electrodes 4, the switch group 10 is opened, the switch group 9 is closed to short circuit the electrodes 3 and the switch 13 is closed to ground the electrodes 3. Thereafter, by closing the switch group 15, the pulser/receiver 16 is connected to the switch group 10 side. Then, the source of high-voltage 18 is connected to the switch group 15 side by switching the switch 17. After the polarization of the vibrator 2 by the high-voltage source 18 under this state, the switch 17 is opened and the rowarrays of electrodes 4 at the switch group 10 side are driven by the pulser/receiver 16.

When the row-arrays of electrodes 4 are driven by the electric pulses, a tomogram of a subject in the array direction of the electrodes 4 is obtained. As the array direction of the electrodes 4 is orthogonal to the array direction of the electrodes 3, a tomogram obtained by the driving the electrodes 4 by electric pulses and a tomogram obtained by driving the electrodes 3 are orthogonal to each other and thus, tomograms at mutually orthogonal and spatially close positions can be obtained.

From the viewpoint of reducing the number of cables connecting the ultrasonic diagnosing system with the ultrasonic probe 1 and to minimize the effect of the capacitive component of the cables, it is desirable to position the switch groups 9, 10, 13 and 15 in the ultrasonic probe 1, but it is also possible to put them at the ultrasonic diagnosing system side.

In this embodiment, the piezoelectric material used in the vibrator is not continuous and the spaces between the vibrator elements are filled with materials having sufficiently less acoustic impedance and therefore, acoustic and electric crosstalk are reduced between the vibrator elements Thus, the ultrasonic wavereceiving sensitivity is improved and more accurate tomograms can be obtained.

Because the vibrators and electrodes are firmly connected by spacer segments 25 of the high molecular material 25 rigidity of the entire probe can be increased and the breakage of electrodes due to deflection of the probe can be avoided.

Figure 5:
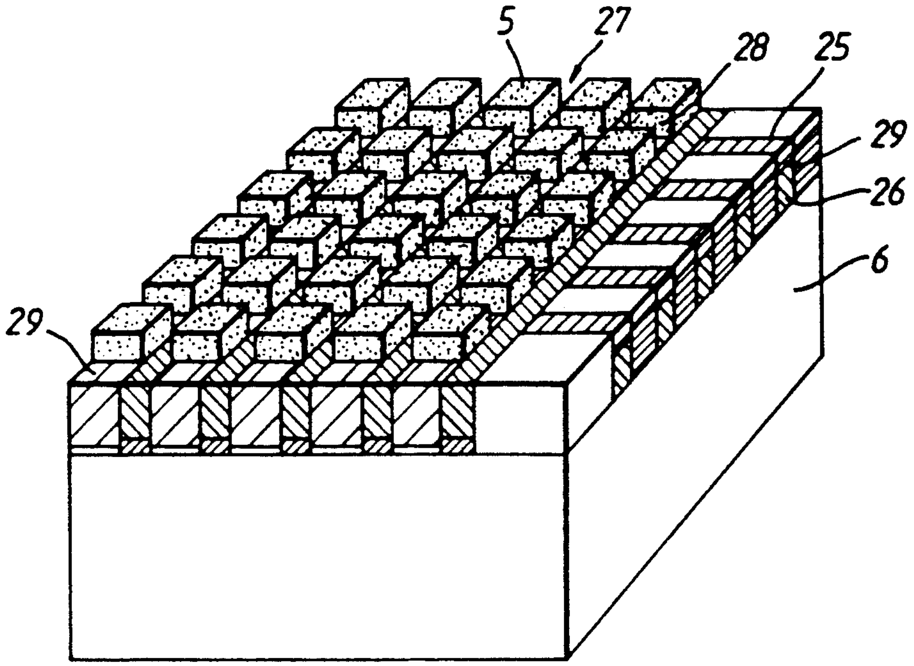

Shown in FIG. 5 is a modification of the ultrasonic probe shown in FIG. 1. To facilitate interconnection with the lead wires from the electrodes, there are provided lead take-out parts 29 extending from the electrodes 3 and 4 to respective sides of the ultrasonic probe. Grooves 27 and 28 are cut in the matching layer 5, where the vibrator 2 piezoelectric material elements are not provided and the matching layer is left only on the part where electrodes 3 may possibly be exposed. These grooves 27 and 28 further reduce acoustic crosstalk between the vibrator elements 2 composing the different arrays and promote accuracy of tomograms.

The driving means as described above is also applied to the case of using the ordinarily plane-type piezoelectric material. In this case, it is possible to get two tomograms at mutually orthogonal and spatially close positions using the probes of the present invention. Depolarization of the piezoelectric material is avoided as electric pulses are always applied in the direction conforming to the polarization direction.

Embodiment 2

Figure 6:
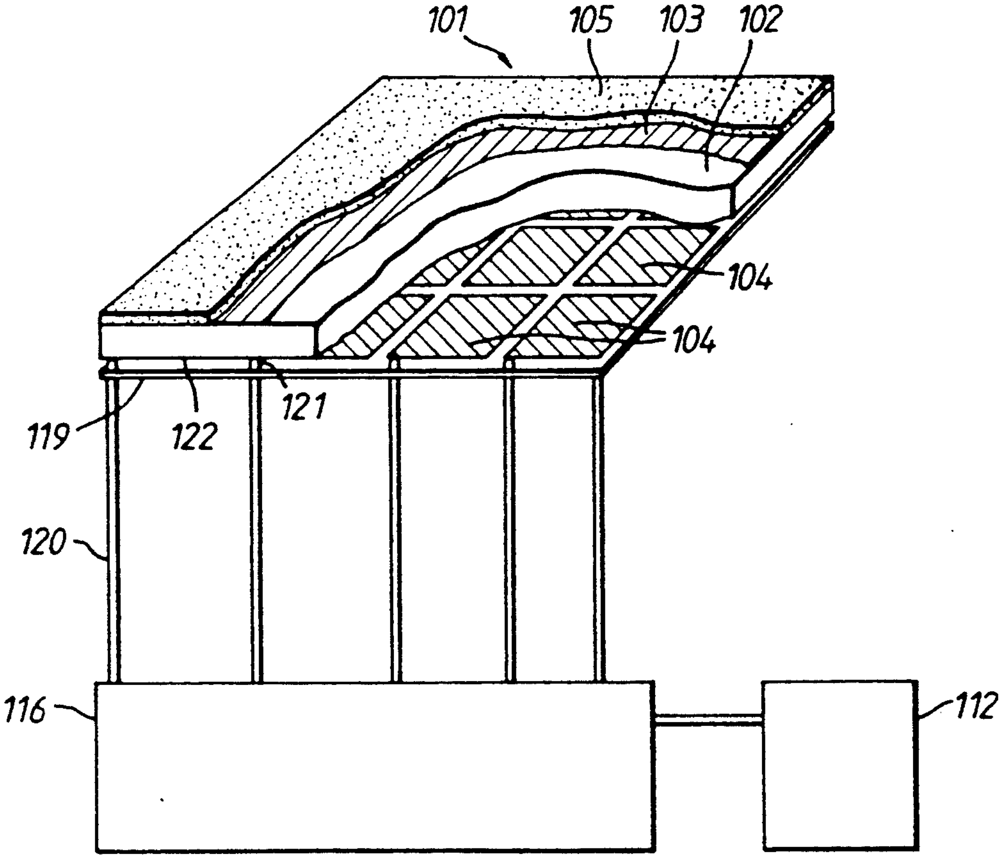

FIG. 6 shows a schematic representation of the construction of another ultrasonic diagnosing system in accordance with the present invention. This ultrasonic diagnosing system includes ultrasonic probe 101 that transmits and receives ultrasonic waves during examination of the subject. Ultrasonic probe 101 includes vibrator 102 made of piezoelectric material, a common electrode 103 provided on the surface of the front side of vibrator 102, electrodes 104 arranged on the back side in the desired matrix shape, and a switch circuit board 119 arranged on the back side of the vibrator 102 to select a combination of electrodes 104 to which electric pulses are applied.

For satisfactory transmission of ultrasonic waves between the vibrator 102 and a subject, the surface of the vibrator has been covered at the common electrode 103 side by a matching layer 105.

The common electrode 103 is grounded and electrodes 104 are connected to the switch circuit board 119 via the connectors 121. The switch circuit board 119 is connected through the cable 120 to the pulser/receiver circuit 116 which is the source of electric pulses.

Figure 7:
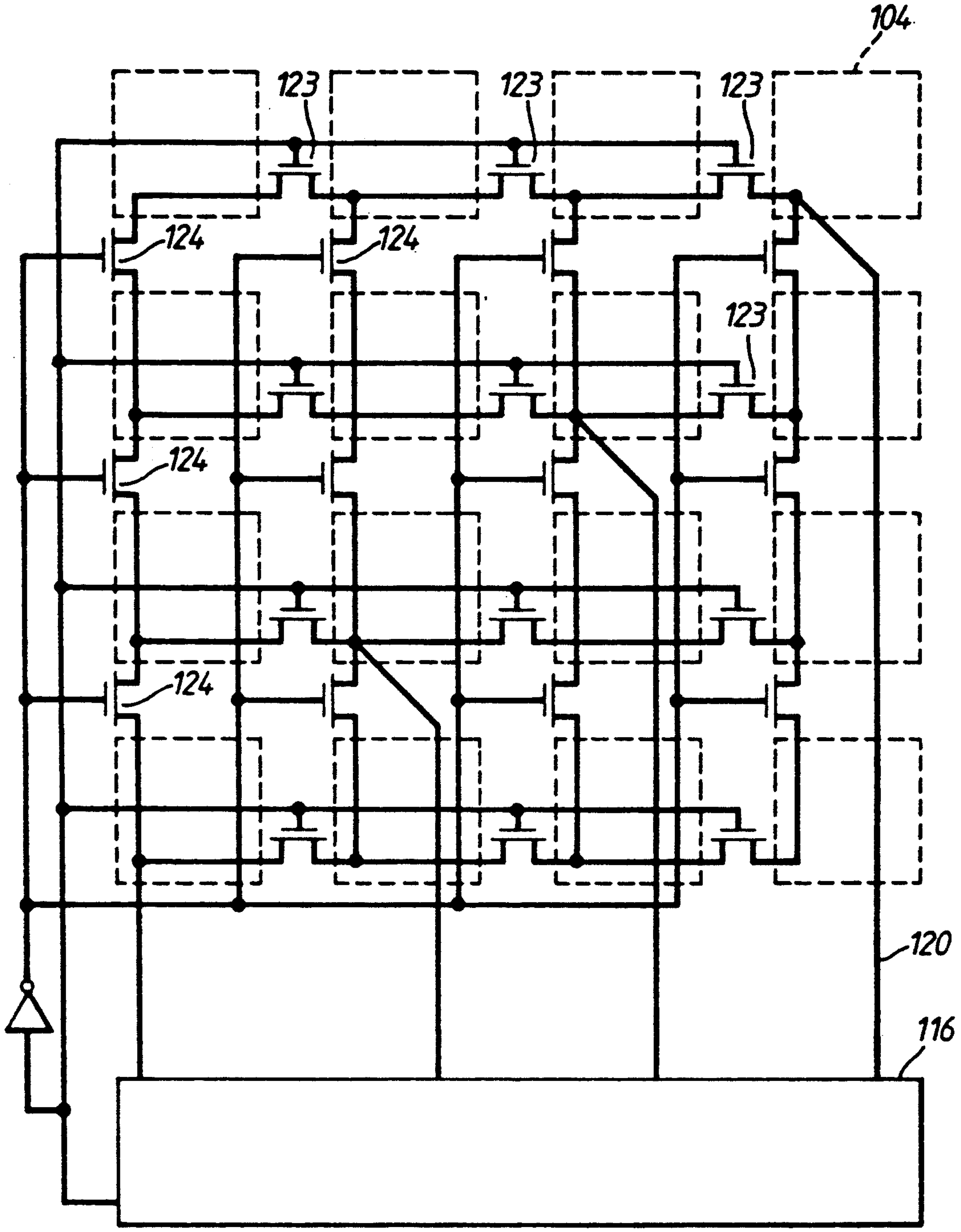
FIG. 7 is a circuit diagram for use in the embodiment of or FIG. 6.

FIG. 7 shows schematically the plan of the switch circuit board 119. As shown in this figure, the switch circuit board 119 has switch group 123 which can short circuit one of the horizontal rows of electrodes 104 at a time and connect it to pulser/receiver circuit 116, and switch group 124 which can short circuit one of the vertical rows of the electrode 104 at a time and connect it to pulser/receiver circuit 116. These switch groups 123 and 124 are so controlled by the control unit 112 that when one of them is closed, another group is open. The cable 120 is connected to the diagonally arranged electrodes 104 and therefore, when the electrodes 104 arranged in the matrix shape are used as the array electrodes in any directions, it is not necessary to change the positions of the electrodes to which the cable 120 is connected.

Because of the air layer 122 formed between the electrodes 104 and the circuit board 119, ultrasonic waves are only weakly incident on the back side of the vibrator. Therefore, it is not necessary to take into consideration the effect of any secondary vibration by the switch circuit board 119, and a backing material layer is not required in this embodiment.

When providing scanning ultrasonic waves in the horizontal direction in FIG. 7 is required, first, the control unit 112 transmits a signal to the switch circuit board 119 so close the switch group 124 and open the switch group 123 of the switch circuit board 119. Upon receipt of this signal, the switch groups 123 and 124 thus cooperate to interconnect the electrodes 104 arranged in the matrix shape to provide rows of electrodes connected only in the vertical direction and to form the array electrodes for scanning in the horizontal direction. This switch operation also connects the formed array electrodes to the pulser/ receiver circuit 116. In this state, it is possible to scan ultrasonic waves in the horizontal array direction by applying electric pulses to the electrodes 104 by the pulser/receiver circuit 116.

When scanning ultrasonic waves in the vertical direction in FIG. 7 are to be provided, first, the control unit 112 transmits a signal to the switch circuit board 119 to close the switch group 123 and open the switch group 124 of the switch circuit board 119. Upon receipt of this signal., the switch groups 123 and 124 cooperate to form interconnected rows of electrodes in the horizontal direction, to form the array electrodes for scanning in the vertical direction. This switch operation also connects the formed array electrodes to the pulser/-receiver circuit 116. In this state, it is possible to scan ultrasonic waves in the vertical array direction by applying electric pulses to the electrodes 104 by the pulser/receiver circuit 116.

The electrodes to which electric pulses are applied are always the electrodes 104 in this embodiment and, therefore, it is unnecessary to change the direction of polarization of the vibrator 102. Furthermore, as the ultrasonic transmission or receiving surface is not the surface contracting a subject, there is a less chance for a subject to get an electric shock.

Embodiment 3

Figure 8:
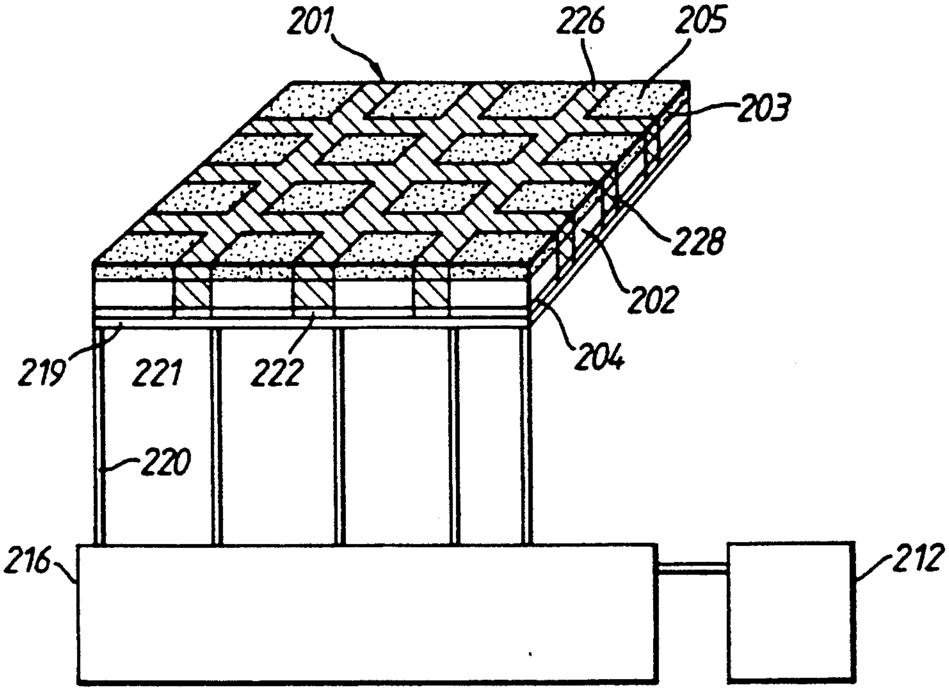
FIG. 8 is an oblique view showing a possible further embodiment of the ultrasonic probe according to the present invention; and, FIG. 9 is an oblique view showing yet another embodiment of the present invention.

FIG. 8 shows a possible further embodiment of the probes of the present invention in which the electrode described in the second embodiment would be combined with the matrix of individual vibrator elements in the form of cube-shaped piezoelectric materials described in the first embodiment. In this case, probe 201 would include common square-shaped electrodes 203 formed on the front side of each of the cube-shaped vibrator elements 202. Square-shaped electrodes 204 would be formed on the back sides of the vibrator elements 202. The vibrator elements 202 would be clamped between the common electrodes 203 and a respective one of the electrodes 204 which would be arranged in the matrix shape as in the second embodiment. In this contemplated third embodiment, individual matching layers 205 would be arranged in the matrix shape to overlie the front sides of the vibrator elements 202, and the spaces between the vibrator 202 and the matching layers 205 would be filled with the filling material 226. Because of this construction, acoustic crosstalk and electric crosstalk between the vibrator elements 202 are expected to be reduced. Further, as the common electrodes 203 would contribute to rigidity of the ultrasonic probe 201 even if the vibrator were split into elements 202, a large amount of the high molecular material for increasing rigidity of the ultrasonic probe 201 may not be required in this embodiment.

Embodiment 4

Figure 9:
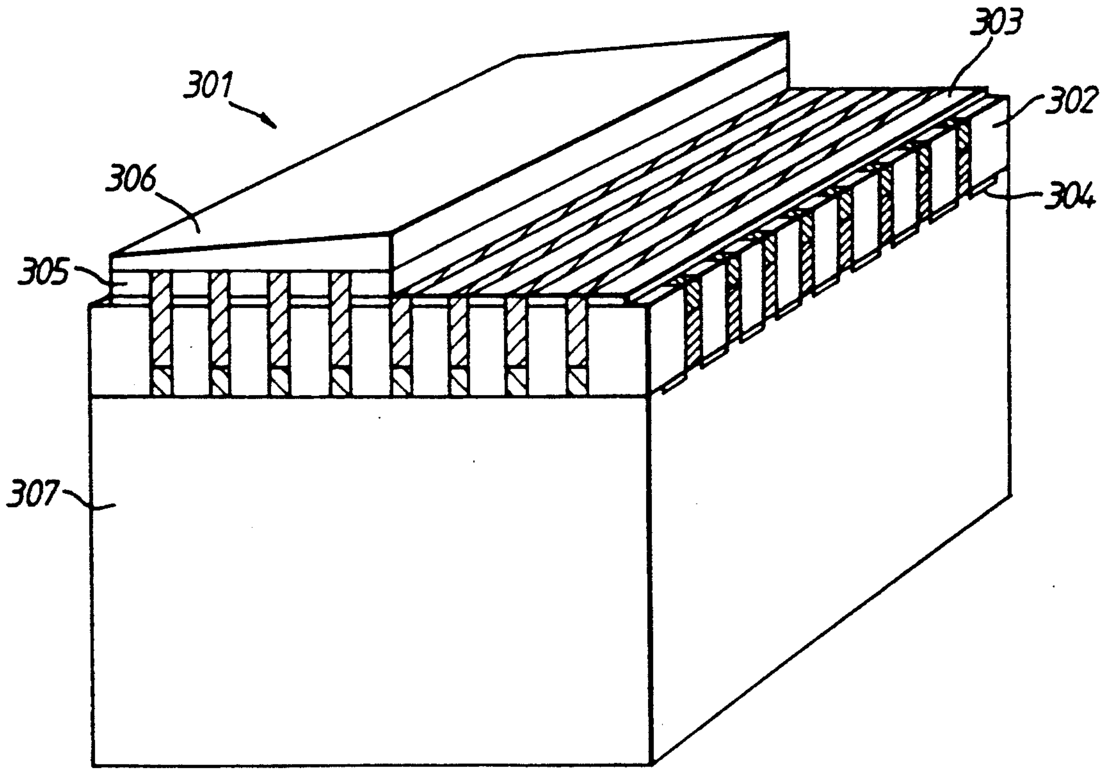

FIG. 9 shows schematically the construction of another embodiment of the probes made in accordance with the present invention. This probe 301 includes vibrator made of a plurality of spaced discrete arrayed vibrator elements 302 of a piezoelectric material. Strip electrodes 303 and 304 are arranged on the front and back sides, respectively of the vibrator elements 302 in multiple rows parallel to each other. The direction of the rows of electrode 303 is orthogonal to the direction of the rows of electrode 304.

A matching layer element 305 is arranged on each element of the electrode 303 to form a matching layer. An acoustic lens 306 is arranged on the matching layer formed by the individual matching layer elements 305.

On the other side, a backing material layer 307 is arranged in contact with the electrodes 304.

The matching layer elements 305 transmit ultrasonic waves between vibrator elements 302 and a subject (not shown) through lens 306, while the backing material layer 307 absorbs ultrasonic waves vibrated toward the back side of the vibrator, similar to operation of embodiment 1.

The construction of the vibrator and electrodes of probe structure of embodiment 4 is similar to that of embodiment 1 shown in FIG. 2(*a*), and 2(*b*).

However, in this embodiment, the matching layer is made of a plurality of discrete, arrayed matching layer elements 305 and the open spaces between the matching layer elements are filled with filling material having below A40 of Shore hardness in JIS and acoustic impedance less than 3 Mrayls.

The material of the filling material on the matching layer side should have high adhesion to the material of the acoustic lens 306, while the material of the filing material on the backing material side should have high adhesion to the material of backing material 307. For example, when the acoustic lens made of silicone resin is used, the material of the filling material on the matching layer side should be selected from the group of silicone filling resins, on the other hand the material of the filling material on the matching material side can be selected from the group of epoxy resins to fit to the backing materials. By the different kinds of filling materials on each side, the adhesion to the acoustic lens or backing material can be easier and stronger and the materials of the acoustic lens and backing material can be selected from more variation.

The method of manufacturing the probe as mentioned above is similar to that of embodiment 1 except using the two kinds of different materials as filling material and after forming the electrodes as shown in FIG. 3(*e*), a matching layer is formed on one electrode side, then the grooves are made in the electrode material and the high molecular material under the electrode and also the matching layer on the electrode together.

In the embodiment, the discrete spacer segments 308 are formed of a high molecular weight material and exhibit above D50 of Shore hardness in JIS, similar to embodiment 1.

The present invention has been described with respect to specific embodiments. However, other embodiments based on the principles of the present invention will be obvious to those of ordinary skill in the art. Such embodiments are in%ended to be covered by the claims.

What is claimed is:

1. An ultrasonic probe comprising:

a vibrator member including a plurality of spaced member elements of a piezoelectric material arranged in a matrix, each of said spaced member elements having front and back opposing surfaces;

first electrode means disposed on the front surfaces of said spaced member elements;

second electrode means disposed on the back surfaces of said spaced member elements; and a plurality of spacer segments disposed between adjacent ones of said spaced member elements, said spacer segments being formed of a high molecular weight material having an acoustic impedance less than that of the piezoelectric material.

2. The ultrasonic probe as in claim 1 wherein the high molecular weight material has a Shore hardness of 50D (JIS) or more.

3. The ultrasonic probe as in claim 1 wherein said spacer segment between each of said adjacent ones of said spaced member elements occupies less than the total volume of space between said adjacent ones of said spaced member elements.

4. The ultrasonic probe as in claim 3 wherein the volume of space between said adjacent ones of said spaced member elements not occupied by said spacer segments is filled with at least one filling material.

5. The ultrasonic probe as in claim 4 wherein the filling material has an acoustic impedance of about 3 Mrayls or less.

6. The ultrasonic probe as in claim 4 wherein the filling material has a Shore hardness of 40A (JIS) or less.

7. The ultrasonic probe as in claim 3 wherein the thickness of said spacer segments in the front-back direction is between about 1/10–½ that of said member elements.

8. The ultrasonic probe as in claim 1 wherein each of said first and second electrode means includes a plurality of strip electrodes electrically interconnecting respective member elements in an array of parallel rows, wherein the direction of the row array defined by said electrodes of said first electrode means is orthogonal to the row array direction defined by said electrodes of said second electrode means.

9. The ultrasonic probe as in claim 8 wherein the thickness of said spacer segments in the front-back direction is between about 1/10–½ that of said member elements, and wherein those of said spacer segments disposed between member elements interconnected by said first electrode means are positioned adjacent the front surfaces of the respective member elements and those of said spacer segments disposed between member elements interconnected by said second electrode means are positioned adjacent the back surfaces of the respective member elements.

10. The ultrasonic probe as in claim 9 wherein said volume of space between said spaced member elements not occupied by said spacer segments is filled with at least one filling material having an acoustic impedance less than about 3 Myrals and a Shore hardness less than about 40A (JIS).

11. The ultrasonic probe as in claim 1 further comprising a matching layer disposed over the front surfaces of said spaced member elements.

12. The ultrasonic probe as in claim 11 wherein said matching layer is comprised of a plurality of matching layer elements, each of said layer elements disposed on the front surface of a respective member element.

13. The ultrasonic probe as in claim 11 further including an acoustic lens disposed on said matching layer.

14. A method for making an vibrator member of an ultrasonic probe, the vibrator member comprised of a plurality of member elements each having opposing front and back surfaces and arranged in a matrix and spaced by spacer segments, a plurality of first electrodes disposed on the front surfaces of the member elements to form a first array of parallel rows of electrically interconnected member elements, a plurality of second electrodes disposed on the back surfaces of the member elements to form a second array of electrically interconnected member elements, the directions of the first and second arrays being mutually orthogonal, the method comprising the steps of:

a) arranging the member elements into the matrix;
b) forming a high molecular weight material in the volume space between adjacent member elements;
c) forming first and second electrode sheets covering the front and back surfaces respectively of the arranged member elements;
d) removing both the portion of the first electrode sheet covering the high molecular weight material between the intended rows of the first array to form the first electrodes, and a portion of the high molecular weight material between the first electrodes, the removed high molecular weight material portion extending to a depth less than the thickness of the member elements, thereby forming the spacer segments between the rows of the first array; and
e) repeating step d) but for the second electrode sheet to form the second electrodes and the spacer segments between the rows of the second array.

15. The method as in claim 14 wherein a filing material is formed in the spaces of the removed high molecular weight material portions, said filling material having an acoustic impedance of 3 Mrayls or less and a Shore hardness of 40A (JIS) or less.

16. An ultrasonic diagnosing system comprising:

a probe having a vibrator member made of piezoelectric material and having a pair of opposing surfaces, a common electrode arranged on one of said surfaces, and a plurality of electrode elements arranged in a matrix pattern on the other of said surfaces; a source of electric pulses; and switching means interconnecting said source and said plurality of electrode elements for selectively connecting the electrode elements to the source in rows arranged alternatively in a first direction or in a second direction orthogonal to said first direction.

17. The ultrasonic diagnosing system as in claim 16 wherein said vibrator member comprises a plurality of spaced member elements arranged in said matrix pattern, and wherein said common electrode comprises a plurality of common electrode elements distributed on said spaced member elements.

18. The ultrasonic diagnosing system as in claim 17 wherein said probe further includes filling material disposed between adjacent ones of said spaced member elements.

19. The ultrasonic diagnosing system as in claim 18 wherein said filling material has a Shore hardness of less than about 40A (JIS).

20. The ultrasonic diagnosing system as in claim 18 wherein said filling material has an acoustic impedance less than about 3 Mrayls.

21. An ultrasonic probe comprising:

a vibrator member comprising a plurality of spaced member elements of a piezoelectric material arranged in a matrix, each of said elements having front and back opposing surfaces;
first electrode means disposed on the front surfaces of said spaced member elements;
second electrode means disposed on the back surfaces of said spaced member elements;
a plurality of spacer segments disposed between adjacent ones of said spaced member elements, said segments being formed o a high molecular weight material having an acoustic impedance less than that of the piezoelectric material;
each of said first and second electrode means including a plurality of strip electrodes electrically interconnecting respective member elements in an array of parallel rows, the direction of the row array defined by said electrodes of said first electrode means being orthogonal to the row array direction defined by said electrodes of said second electrode means, wherein the thickness of said spacer segments in the front-back direction is between about 1/10–½ that of said spaced member elements, and further wherein those of said spacer segments disposed between member elements interconnected by said first electrode means are positioned adjacent the front surfaces of the respective member elements and those of said spacer segments disposed between member elements interconnected by said second electrode means are positioned adjacent the back surfaces of the respective member elements.

22. The ultrasonic probe as in claim 21, wherein the volume of space between said spaced member elements not occupied by said spacer segments is filled with at least one filling material having an acoustic impedance less than about 3 Mrayls and a Shore hardness less than about 40A (JIS).

* * * * *

UNITED STATES PATENT AND TRADEMARK OFFICE

CERTIFICATE OF CORRECTION

PATENT NO. : 5,327,895

DATED : July 12, 1994

INVENTOR(S) : Shinichi HASHIMOTO et al.

It is certified that error appears in the above-indentified patent and that said Letters Patent is hereby corrected as shown below:

Abstract, Title Page, Line 3, delete ";".

Claim 10, Column 11, Line 21, change "Myrals" to --Mrayls--.

Claim 14, Column 11, Line 32, change "an" to --a--.

Claim 21, Column 12, Line 40, change "o" to --of--.

Signed and Sealed this

Twenty-eight Day of February, 1995

*Attest:*

BRUCE LEHMAN

*Attesting Officer*

*Commissioner of Patents and Trademarks*